United States Patent
Lee et al.

(10) Patent No.: US 8,703,986 B1
(45) Date of Patent: Apr. 22, 2014

(54) PROCESS FOR PREPARING 10-CHLORO-9, 10-DIHYDRO-9-OXA-10-PHOSPHAPHENANTHRENE-10-OXIDE COMPOUND

(71) Applicant: UFC Corporation, Taipei (TW)

(72) Inventors: Yu-Chin Lee, Taipei (TW); Jen-Hai Liao, Taipei (TW); Sung-Chen Lo, Taipei (TW); Chu-Chun Wu, Taipei (TW)

(73) Assignee: UFC Corporation, Taipei (TW)

( * ) Notice: Subject to any disclaimer, the term of this patent is extended or adjusted under 35 U.S.C. 154(b) by 0 days.

(21) Appl. No.: 13/932,111

(22) Filed: Jul. 1, 2013

(51) Int. Cl.
*C07F 9/02* (2006.01)

(52) U.S. Cl.
USPC .......................................................... 558/82

(58) Field of Classification Search
USPC .......................................................... 558/82
See application file for complete search history.

(56) References Cited

U.S. PATENT DOCUMENTS 7,232,921 B2   6/2007  Su et al.
7,626,051 B2  12/2009  Su et al.

OTHER PUBLICATIONS

Jorg Gloede, et al. "A stable Trichloro-oxyphosphorane with an Oxaphosphorine Ring", Z. Anorg. Allg. Chem. 2003, 629, 998-1000. Weinheim.

*Primary Examiner* — Kristin Vajda
(74) *Attorney, Agent, or Firm* — Fishman & Associates, LLC.

(57) ABSTRACT

Provided is a process for preparing 10-chloro-9,10-dihydro-9-oxa-10-phosphaphenanthrene-10-oxide (DOPO-C) compound, the process having steps of:

reacting a liquid chlorinating agent and 9,10-dihydro-10-hydroxy-9-oxa 10-phosphaphenanthrene 10-oxide compound represented by formula (B) to form a mixture, the mixture comprises DOPO-C compound represented by formula (A) and an unreacted liquid chlorinating agent,

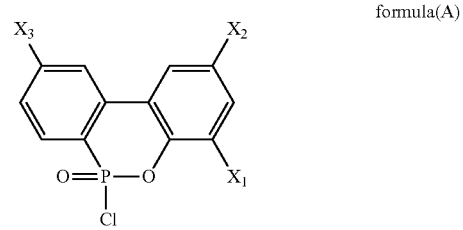
formula(A)

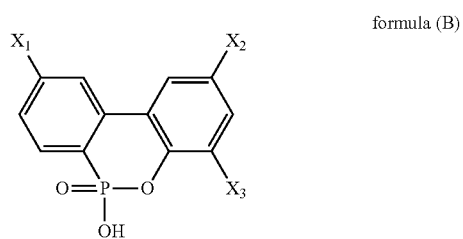

formula (B)

separating the DOPO-C compound and the unreacted liquid chlorinating agent from the mixture to obtain the DOPO-C compound; wherein $X_1$, $X_2$, and $X_3$ are each independently selected from the group consisting of hydrogen atom, hydroxyl group, cyano group, sulfonic acid group, sulfonate ester group represented by $—SO_3R_1$, halogen atom, alkoxy group represented by $—OR_2$, acyclic hydrocarbon group having 1 to 8 carbon atoms, cyclic alkyl group having 3 to 8 carbon atoms, aryl group, heteroaryl group, and arylalkyl group, wherein $R_1$ and $R_2$ are each an acyclic hydrocarbon group having 1 to 8 carbon atoms.

20 Claims, No Drawings

PROCESS FOR PREPARING 10-CHLORO-9, 10-DIHYDRO-9-OXA-10-PHOSPHAPHENANTHRENE-10-OXIDE COMPOUND

BACKGROUND OF THE INVENTION

1. Field of the Invention

The present invention relates to a process for preparing a phosphorus-containing compound, particularly to a process for preparing 10-chloro-9,10-dihydro-9-oxa-10-phosphaphenanthrene-10-oxide compound.

2. Description of the Prior Arts

As public environmental awareness increases, many halogen-containing flame retardants have been gradually replaced by halogen-free compounds to avoid producing highly toxic and corrosive gases during combustion of polymers that contain halogen type flame retardants. The halogen-free compounds are commonly used to improve the properties of the obtained polymers such as flame retardancy and heat resistance, and the halogen-free compounds also render the obtained polymers more environmentally friendly.

One of the most widely studied halogen-free compounds is 9,10-dihydro-9-oxa-10-phosphaphenanthrene-10-oxide (DOPO), a phosphorus-containing compound which can be used as a phosphorus based flame retardant. However, DOPO and its derivatives are well suited only for limited polymers. In order to further expand the application of DOPO that can be successfully applied in various kinds of polymers, researchers have been focused on developing various derivatives of DOPO.

One of the derivatives of DOPO is 10-chloro-9,10-dihydro-9-oxa-10-phosphaphenanthrene-10-oxide (abbreviated as DOPO-C or CDOPO), which also itself can be used as a phosphorus based flame retardant and is a reactive flame retardant intermediate as well. By reacting of DOPO-C with polymers, a halogen-free flame retardant system can be thus produced. For example, a phosphorus-containing phenolic resin can be obtained by reacting DOPO-C with phenol formaldehyde resin, which can be used as a non-halogenated curing agent for copper clad laminate and printed circuit board industries.

Accordingly, due to the promising and potential applications of DOPO-C for electrical and electronic industries, researchers from academia and industry have been improving and developing new synthetic processes of DOPO-C. As disclosed in U.S. Pat. No. 7,232,921, a method for preparing a biphenylphosphonate compound involves oxidizing 6-chloro-6H-dibenz[c,e][1,2]oxaphosphorin (CDOP) by using ozone under heat, so as to obtain DOPO-C. However, the drawbacks of the method disclosed by the prior art include: complicated precision instruments are required for preparing ozone and adjusting ozone in amount, thereby remarkably increasing the difficulty of preparation; and excessive exposure to hazardous ozone gas will harm the respiratory system, mucous membrane and eyes. Therefore, because of the costly precision instruments, complexity in operating the precision instruments, and chemical hazard, the conventional method is not applicable for mass production of DOPO-C.

Besides, Jörg Gloede et. al. (*Z. Anorg. Allg. Chem.* 2003, 629, 998-1000), disclosed a method for preparing DOPO-C. CDOP is reacted with chlorine in chloroform at a low temperature of −20° C. at first, and DOPO-C is obtained after hydrolysis reaction. However, the drawbacks of the method disclosed by the prior art include: a low yield of only 76%; the difficulty in operation of gaseous chlorine; and irritation of the respiratory system by chlorine, all of which result in harming health and safety of workers, and may further lead to death; and a requirement of precision instruments such as low temperature thermostatic sinks since a low temperature condition is needed in the course of preparing DOPO-C. Therefore, the aforementioned disadvantages lower the industrial application of the method and render the method unsuitable for mass production of DOPO-C as well.

To overcome the shortcomings, the present invention provides a process for preparing 10-chloro-9,10-dihydro-9-oxa-10-phosphaphenanthrene-10-oxide (DOPO-C) compound to mitigate or obviate the aforementioned problems.

SUMMARY OF THE INVENTION

Given that the aforesaid drawbacks of the prior art such as chemical hazard, requirements of costly but indispensable precision instruments, and complexity in operation of the precision instruments, the main objective of the present invention is to provide a process for preparing 10-chloro-9,10-dihydro-9-oxa-10-phosphaphenanthrene-10-oxide (DOPO-C) compound, particularly, a process that is safe and easy in operation without involving costly precision instruments, and more particularly, a process applicable to mass production of the DOPO-C compound.

Accordingly, the present invention provides a process for preparing 10-dihydro-9-oxa-10-phosphaphenanthrene-10-oxide (DOPO-C) compound, wherein the DOPO-C compound is represented by formula (A):

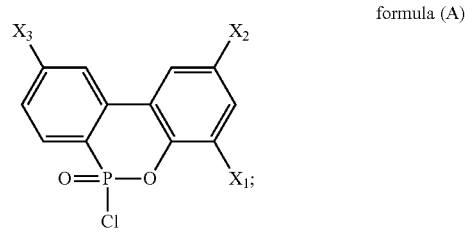

formula (A)

and the process in accordance with the present invention comprises steps of:

reacting a liquid chlorinating agent and 9,10-dihydro-10-hydroxy-9-oxa-10-phosphaphenanthrene 10-oxide (DOPO-OH) compound represented by formula (B) to form a mixture, wherein the mixture comprises the DOPO-C compound represented by formula (A) and an unreacted liquid chlorinating agent,

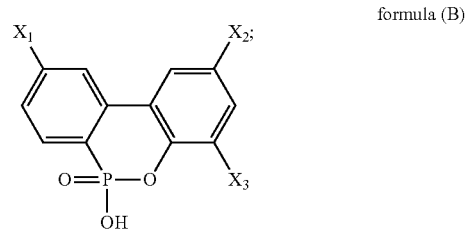

formula (B)

and separating the DOPO-C compound represented by formula (A) and the unreacted liquid chlorinating agent from the mixture, so as to obtain the DOPO-C compound represented by formula (A); wherein the variables $X_1$, $X_2$, and $X_3$ are each independently selected from the group consisting of hydrogen atom, hydroxyl group, cyano group, sulfonic acid group, sulfonate ester group represented by —$SO_3R_1$, halogen atom, alkoxy group represented by —$OR_2$, acyclic hydrocarbon group having 1 to 8 carbon atoms, cyclic alkyl group having 3 to 6 carbon atoms, aryl group, heteroaryl group, and arylalkyl group, wherein $R_1$ and $R_2$ are each independently an acyclic hydrocarbon group having 1 to 8 carbon atoms.

According to the present invention, the liquid chlorinating agent refers to any reagent able to add a chlorine atom to an organic compound such as the DOPO-OH compound of the present invention through any kind of reaction such as substitution or replacement. Furthermore, the liquid chlorinating agent is liquid at room temperature, wherein the room temperature is, but not limited to, ranging from 15° C. to 40° C. The liquid chlorinating agent includes, but is not limited to, thionyl chloride ($SOCl_2$), phosphorus oxychloride ($POCl_3$), phosphorus trichloride, ($PCl_3$), oxalyl chloride (($COCl)_2$) or any other suitable reagent.

According to the present invention, the term "acyclic hydrocarbon group having 1 to 8 carbon atoms" refers to a linear hydrocarbon-group having 1 to 8 carbon atoms or a branched hydrocarbon group having 1 to 8 carbon atoms. The term "hydrocarbon group" refers to a saturated hydrocarbon group or an unsaturated hydrocarbon group. The term "linear hydrocarbon group having 1 to 8 carbon atoms" further refers to a linear alkyl group having 1 to 8 carbon atoms, a linear alkenyl group having 2 to 8 carbon atoms, or a linear-chain alkynyl group having 2 to 8 carbon atoms. The term "branched hydrocarbon group having 1 to 8 carbon atoms" further refers to a branched alkyl group having 1 to 8 carbon atoms, a branched alkenyl group having 2 to 8 carbon atoms, or a branched alkynyl group having 2 to 8 carbon atoms.

According to the present invention, the acyclic hydrocarbon group having 1 to 8 carbon atoms includes, but is not limited to, methyl group, ethyl group, n-propyl group, 2-propyl group, n-butyl group, 1-methylpropyl group, 2-methylpropyl group, 1,1-dimethylethyl group, 2-methylbuytl group, 3-methylbutyl group, 2,2-dimethylpropyl group, 1-ethylpropyl group, 1,1-dimethylpropyl group, 1,2-dimethylpropyl group, 1-methylpentyl group, 2-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl group, n-pentyl group, 2-ethylbutyl group, 1-methylbutyl group, 1-ethyl-1-methylpropyl group, n-hexyl group, 1,1,2-trimethylpropyl group, 3-methylpentyl group, allyl group, 1,2-dimethyl-3-butenyl, 1-propenyl group, 1-ethyl-2-methyl-1-propenyl, 2-butenyl group, 1,3-butadienyl group, 2-methyl-3-pentenyl group, 2,2-dimethyl-3-butenyl group, 4-hexenyl group, ethynyl group, 3-methyl-4-pentynyl group, 4-methyl-1-pentynyl group, 3-butynyl group, 2,2-dimethyl-3-butynyl group, 1-ethyl-1-methyl-2-propynyl group, 3-methyl-1-butynyl group, 2-propynyl group, 2-penten-4-ynyl group, 3-methyl-3-butenyl group, and 2-hexynyl group.

According to the present invention, the sulfonate ester group includes, but is not limited to, sulfonic acid ethyl ester group and sulfonic acid methyl ester group.

According to the present invention, the alkoxy group represented by —$OR_2$ includes, but is not limited to, methoxy group, ethoxy group, propoxy group, 1-methylethoxy group, butoxy group, 1-methylpropoxy group, 2-methylpropoxy group, 1,1-dimethylethoxy group, pentoxy group, 1-methylbutoxy group, 2-methylbutoxy group, 3-methoxybutoxy group, 1,1-dimethylpropoxy group, 1,2-dimethylpropoxy group, 1-ethylpropoxy group, hexoxy group, 1-methylpentoxy group, 2-methylpentoxy group, 3-methylpentoxy group, 4-methylpentoxy group, 1,1-dimethylbutoxy group, 1,2-dimethylbutoxy group, 1,3-dimethylbutoxy group, 2,2-dimethylbutoxy group, 2,3-dimethylbutoxy group, 1-ethylbutoxy group, 2-ethylbutoxy group, 1,1,2-trimethylpropoxy group, 1,2,2-tri-methylpropoxy group, 1-ethyl-1-methylpropoxy group and 1-ethyl-2-methylpropoxy group.

According to the present invention, the $C_3$-$C_6$ cyclic alkyl group includes, but is not limited to, cyclohexyl group, cyclopentyl group, cyclobutyl group, and cyclopropyl group.

According to the present invention, the aryl group has any substituent and includes, but is not limited to, phenyl group, naphthyl group, anthracenyl group, biphenyl group, p-chlorophenyl group, and p-methoxyphenyl group, and p-fluorophenyl group.

According to the present invention, the heteroaryl group refers to an aromatic compound having at least one non-carbon atom in the aromatic ring, including, but not limited to, pyridine group, pyrrole group, furan group, and thiophene group.

According to the present invention, the arylalkyl group has any substituent and includes, but is not limited to, benzyl, p-chlorobenzyl group, p-methoxybenzyl group and p-fluorobenzyl group.

According to the present invention, the method for separating the DOPO-C compound represented by formula (A) and the unreacted liquid chlorinating agent from the mixture includes, but is not limited to, distillation, column chromatography and any other suitable method. The suitable method may depend on the liquid chlorinating agent. For example, when the liquid chlorinating agent is thionyl chloride, the preferable method for separating the DOPO-C compound represented by formula (A) and the unreacted liquid chlorinating agent from the mixture is distillation.

According to the present invention, the reaction time of the step of reacting a liquid chlorinating agent and DOPO-OH compound to form a mixture varies under different conditions including, but not limited to, amount of the liquid chlorinating agent, amount of the DOPO-OH compound, and reaction temperatures. The reaction time is, but not limited to, over 10 hours.

According to the present invention, the yield of the DOPO-C compound prepared by the present invention is over 80%. Preferably, the yield is over 85%. More preferably, the yield is over 90%. Further preferably, the yield is over 95%.

Accordingly, the process for preparing a DOPO-C compound of the present invention has the following advantages:

(1) The process simply involves a step of reacting a liquid chlorinating agent and DOPO-OH compound and a step of separating the DOPO-C compound represented by formula (A) and the unreacted liquid chlorinating agent; therefore the process is much simplified. Besides, the liquid chlorinating agent is in liquid form at room temperature, so during the course of the process, the hazard of operating a gaseous reagent at room temperature and complexity in operation of the costly precision instruments can be avoided. Thus, the process of the present invention is easy in operation, and is safe and cost-effective.

(2) The unreacted liquid chlorinating agent can be reused, such that the process is further cost-effective.

(3) The reaction between a liquid chlorinating agent and DOPO-OH compound is very mild, and thereby a low reaction temperature, such as lower than −10° C., is not needed. Accordingly, the present invention does not involve precision instruments such as low temperature thermostatic sinks; hence the process further reduces the cost of instruments.

(4) The yield of the DOPO-C compound prepared by the present invention is higher than 90%, even higher than 95%.

(5) Since the process of the present invention is safe, cost-effective, and easy to operate, the process is applicable for mass production and further increases industrial applicability.

Preferably, the liquid chlorinating agent is thionyl chloride.

Preferably, after the step of separating the DOPO-C compound represented by formula (A) and the unreacted liquid chlorinating agent from the mixture, the process of the present invention further comprises a step of re-purifying the DOPO-C compound represented by formula (A).

According to the present invention, the method for re-purifying the DOPO-C compound represented by formula (A) includes, but is not limited to reduced pressure distillation. Preferably, the method is distillation at reduced pressure.

Accordingly, the process of the present invention is suitable for mass production for DOPO-C compound of high yield and high purity. Furthermore, since the preferable method for re-purifying the DOPO-C compound represented by formula (A) is distillation at reduced pressure, which is a simple operation, the process of the present invention avoids a waste of solvent and time.

Preferably, the step of reacting a liquid chlorinating agent and DOPO-OH compound to form a mixture includes reacting a liquid chlorinating agent and DOPO-OH compound to form a mixture at a temperature ranging from 50° C. to 130° C.

According to the present invention, the step of reacting a liquid chlorinating agent and DOPO-OH compound to form a mixture at a temperature ranging from 50° C. to 130° C. increases the reaction rate of the liquid chlorinating agent and the DOPO-OH compound.

According to the present invention, the method of "reacting a liquid chlorinating agent and DOPO-OH compound to form a mixture at a temperature ranging from 50° C. to 130° C." refers to any method for heating the chlorinating agent and the DOPO-OH compound, for example, but not limited to, using a water bath or an oil bath. Preferably, the temperature may be adjusted according to the liquid chlorinating agent. For example, but not limited to, when the liquid chlorinating agent is thionyl chloride, oxalyl chloride or phosphorus trichloride, heating under reflux is adopted to react thionyl chloride, oxalyl chloride or phosphorus trichloride and DOPO-OH compound to form a mixture at a temperature ranging from 60° C. to 80° C.; or when the liquid chlorinating agent is phosphorus oxychloride, heating by an oil bath is adopted to react phosphorus oxychloride and DOPO-OH compound to form a mixture at a temperature ranging from 80° C. to 100° C.; or when the liquid chlorinating agent is phosphorus oxychloride, heating under reflux is adopted to react phosphorus oxychloride and DOPO-OH compound to form a mixture at a temperature ranging from 100° C. to 130° C.

Preferably, the equivalent of the liquid chlorinating agent is at least 1/Y when the equivalent of the DOPO-OH compound is 1, wherein Y represents an equivalent of chlorine of the liquid chlorinating agent that reacts with one equivalent of the DOPO-OH compound.

According to the present invention, the DOPO-OH compound is the limiting reagent in the step of reacting a liquid chlorinating agent and DOPO-OH compound to form a mixture.

According to the present invention, the term "an equivalent of chlorine of the liquid chlorinating agent that reacts with one equivalent of the DOPO-OH compound" refers to the amount of chlorine atoms of the liquid chlorinating agent adding to 1 equivalent of the DOPO-OH compound through any kind of reaction such as substitution. For example, but not limited to, when the liquid chlorinating agent is thionyl chloride or oxalyl chloride, the equivalent of chlorine of the liquid chlorinating agent that reacts with one equivalent of the DOPO-OH compound is 2, and thus the equivalent ratio of the DOPO-OH compound to the liquid chlorinating agent is at least ½. When the liquid chlorinating agent is phosphorus trichloride or phosphorus oxychloride, the equivalent of chlorine of the liquid chlorinating agent that reacts with one equivalent of the DOPO-OH compound is 3, and thus the equivalent of the DOPO-OH compound to the liquid chlorinating agent is at least ⅓.

More preferably, the equivalent of the liquid chlorinating agent ranges from 1/Y to 10 when the equivalent of the DOPO-OH compound is 1.

Accordingly, since the equivalent of the liquid chlorinating agent ranges from 1/Y to 10 when the equivalent of the DOPO-OH compound is 1, the reaction of the DOPO-OH compound and the liquid chlorinating agent is complete, resulting in an excellent yield of the DOPO-C compound and thus preventing waste of the liquid chlorinating agent.

Preferably, before the step of reacting a liquid chlorinating agent and DOPO-OH compound to form a mixture, the process of the present invention further comprises steps of:

reacting water and 9,10-dihydro-9-oxa-10-phosphaphenanthrene-10-oxide (DOPO) compound to form an aqueous solution, wherein the DOPO compound is represented by formula (C);

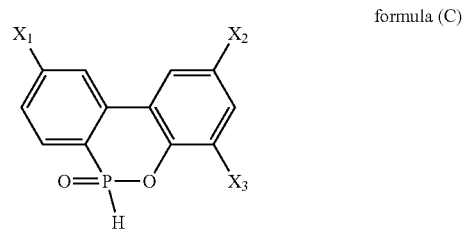

formula (C)

adding a metal-free oxidant into the aqueous solution, so as to obtain a mixed solution, wherein the mixed solution comprises the DOPO-OH compound represented by formula (B); and separating the DOPO-OH compound represented by formula (B) from the mixed solution, so as to obtain the DOPO-OH compound; wherein the variables $X_1$, $X_2$, and $X_3$ are each independently selected from the group consisting of hydrogen atom, hydroxyl group, cyano group, sulfonic acid group, sulfonate ester group represented by —$SO_3R_1$, halogen atom, alkoxy group represented by —$OR_2$, acyclic hydrocarbon group having 1 to 8 carbon atoms, cyclic alkyl group having 3 to 8 carbon atoms, aryl group, heteroaryl group, and arylalkyl group, wherein $R_1$ and $R_2$ are each independently an acyclic hydrocarbon group having 1 to 8 carbon atoms.

According to the present invention, the term "metal-free oxidant" refers to any reagent that does not have any metal element and is able to oxidize another reactant, wherein the metal element is, but not limited to, sodium and potassium. The metal-free oxidant includes, but is not limited to, hydrogen peroxide, oxygen, ozone, halogen, hypochloric acid, chloric acid, perchloric acid, and peracetic acid.

According to the present invention, the reaction time of the step of reacting water and DOPO compound to form an aqueous solution varies under different conditions including, but not limited to, amount of water, amount of the DOPO compound, and reaction temperatures. The reaction time is preferably, but not limited to, 0.5 hour.

According to the present invention, the time of adding a metal-free oxidant into the aqueous solution is adjustable, according to reaction conditions such as the amount of water, the amount of the DOPO compound, and the reaction temperature involved in the reaction. Preferably, the step of adding a metal-free oxidant into the aqueous solution includes adding a metal-free oxidant into the aqueous solution slowly, for example, but not limited to, when the amount of the aqueous solution is about 1000 grams, the time of adding an excessive amount of metal-free oxidant into the aqueous solution is over 2 hours.

More preferably, before the step of separating the DOPO-OH compound represented by formula (B) from the mixed solution, the process of the present invention further comprises a step of allowing the mixed solution to stand for several hours, such as, but not limited to, 3 hours, so as to complete the reaction.

According to the present invention, the method for separating the DOPO-OH compound represented by formula (B) from the mixed solution includes, but is not limited to, recrystallization.

According to the present invention, the process for preparing the DOPO-C compound from DOPO compound results in a high yield of higher than 70%. Preferably, the yield is higher than 75%. More preferably, the yield is higher than 80%. Further preferably, the yield is higher than 85%.

Accordingly, since the course of preparing DOPO-OH compound from DOPO compound of the present invention does not involve any oxidant having metal element, no metal salt is produced during the process, and thus tedious purification for removing the metal salts is no longer required. Hence, the process of the present invention is simplified. Furthermore, the process of the present invention prepares the DOPO-OH compound with a high yield of higher than 90%, and the obtained DOPO-OH compound is with high a purity of 99%. The obtained DOPO-OH compound is then reacted with a liquid chlorinating agent, and the DOPO-C compound represented by formula (A) is obtained after separating the DOPO-C compound from the mixture. Accordingly, the process of the present invention prepares DOPO-C compound from easily accessible DOPO compound with many advantages such as avoiding chemical hazard and thus avoiding harm to the workers, without involving costly precision instruments and thus being cost-effective, and obtaining DOPO-C compound with a high yield and a high purity. Therefore, the process of the present invention is applicable for mass production of DOPO-C compound and further increases the industrial applicability of DOPO-C compound.

Preferably, before the step of reacting water and DOPO compound to form an aqueous solution, the process further comprises steps of: providing the DOPO compound; and heating the DOPO compound to a temperature ranging from 100° C. to 180° C. to render the DOPO compound in liquid form; more preferably, heating the DOPO compound to a temperature ranging from 120° C. to 150° C. to render the DOPO compound in liquid form.

According to the present invention, the step of heating the DOPO compound to a temperature ranging from 100° C. to 180° C. to render the DOPO compound in liquid form facilitates and accelerates the following step of reacting water and the DOPO compound to form an aqueous solution.

Preferably, the step of reacting water and DOPO compound to form an aqueous solution includes reacting water and the DOPO compound to form an aqueous solution at a temperature ranging from 90° C. to 110° C.

According to the present invention, the step of reacting water and the DOPO compound to form an aqueous solution at a temperature ranging from 90° C. to 110° C. accelerates the reaction rate of water and the DOPO compound and maintains a homogenous reaction.

Preferably, the step of adding a metal-free oxidant into the aqueous solution to obtain a mixed solution, is conducted at a temperature ranging from 90° C. to 110° C.

According to the present invention, the step of adding a metal-free oxidant into the aqueous solution, so as to obtain a mixed solution at a temperature ranging from 90° C. to 110° C., accelerates the reaction of the metal-free oxidant and the aqueous solution and prevents the metal-free oxidant from accumulating during the reaction, and thus avoiding chemical hazard.

More preferably, before the step of separating the DOPO-OH compound represented by formula (B) from the mixed solution, the process of the present invention further comprises a step of allowing the mixed solution to stand for several hours at a temperature ranging from 90° C. to 110° C., such as, but not limited to, 3 hours, so as to complete the reaction and shorten the reaction time.

Preferably, the metal-free oxidant is selected from the group consisting of hydrogen peroxide, oxygen, ozone, halogen, hypochloric acid, chloric acid, perchloric acid, peracetic acid and a combination thereof.

According to the present invention, the term "halogen" refers to fluorine ($F_2$), chlorine ($Cl_2$), and bromine ($Br_2$).

Preferably, the equivalent ratio of water to the DOPO compound in the step of reacting water and DOPO compound to form an aqueous solution is at least 1. More preferably, the equivalent ratio of water to the DOPO compound is ranging from 5 to 50.

According to the present invention, the DOPO compound is the limiting reagent in the step of reacting water and DOPO compound to form an aqueous solution.

Preferably, the equivalent ratio of the metal-free oxidant to the DOPO compound in the step of reacting water and DOPO compound to form an aqueous solution is at least 1. More preferably, the equivalent ratio of the metal-free oxidant to the DOPO-OH compound in the step of reacting water and DOPO compound to form an aqueous solution ranges from 1 to 5.

Preferably, the metal-free oxidant is in any form, including, but not limited to, liquid. More preferably, the metal-free oxidant is, but not limited to, 30% hydrogen peroxide solution.

Other objectives, advantages and novel features of the invention will become more apparent from the following detailed description when taken in conjunction with the accompanying drawings.

DETAILED DESCRIPTION OF THE PREFERRED EMBODIMENTS

The present invention provides solutions to solve the problems of the conventional processes for preparing DOPO-C compound. A process for preparing DOPO-C compound from DOPO compound is provided as a preferred embodiment for illustrating but not limiting the scope of the present invention.

The present invention is further illustrated by the following example; it should be understood that the example and embodiment described herein are for illustrative purposes only and should not be construed as limiting the embodiments set forth herein.

The materials and instruments involved in the embodiment of the present invention are as follows:

9,10-dihydro-9-oxa-10-phosphaphenanthrene-10-oxide: purity thereof is 99%.

Hydrogen peroxide solution: concentration thereof is 30%.

Thionyl chloride: purity thereof is 99%.

Embodiment

The process for preparing 10-dihydro-9-oxa-10-phosphaphenanthrene-10-oxide (DOPO-C) compound represented by formula (A) from 9,10-dihydro-9-oxa-10-phosphaphenanthrene-10-oxide (DOPO) compound is as follows, wherein $X_1$, $X_2$, and $X_3$ were hydrogen atoms in the present embodiment.

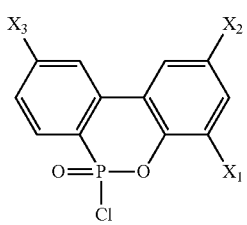

formula (A)

(1) Preparation of 9,10-dihydro-10-hydroxy-9-oxa 10-phosphaphenanthrene 10-oxide (DOPO-OH) compound from DOPO compound 9,10-dihydro-9-oxa-10-phosphaphenanthrene-10-oxide (DOPO) compound represented by formula (C) was provided, wherein $X_1$, $X_2$, and $X_3$ were hydrogen atoms in the present embodiment.

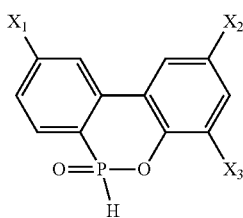

formula (C)

500 grams of the DOPO compound was charged into a three-necked round bottle. The three-necked round bottle was heated to a temperature of about 140° C. to warm the DOPO compound, so as to render the DOPO compound in liquid form. 625 grams of water was added slowly into the three-necked round bottle to mix with the DOPO compound to obtain an aqueous solution at a temperature above 90° C. The aqueous solution was allowed to stand for 30 minutes at a temperature ranging from 90° C. to 100° C., and an excessive amount of hydrogen peroxide solution was slowly added into the aqueous solution over 2 hours to form a mixed solution at a temperature ranging from 90° C. to 100° C. After that, the mixed solution was allowed to stand for 2 hours at a temperature ranging from 90° C. to 100° C.

The mixed solution was then cooled to room temperature and a solid was produced in the mixed solution, wherein the solid was 9,10-dihydro-10-hydroxy-9-oxa 10-phosphaphenanthrene 10-oxide (DOPO-OH) compound represented by formula (B), and the solid was obtained by being separated from the mixed solution by filtering, wherein $X_1$, $X_2$, and $X_3$ were hydrogen atoms in the present embodiment.

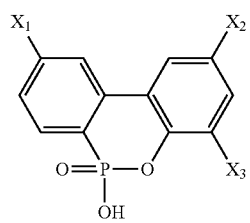

formula (B)

The solid was then washed by water and dried at 80° C. under reduced pressure, and finally 494 grams of dried DOPO-OH compound was obtained, wherein the yield was 92% and the purity of the DOPO-OH compound is 99.5%, which was determined by high-performance liquid chromatography.

(2) Preparation of DOPO-C Compound from DOPO-OH Compound 480 grams of DOPO-OH compound was provided and was mixed with thionyl chloride to form a mixture. The mixture was heated to a temperature ranging from 70° C. to 80° C. over 18 hours by heating under reflux to complete the reaction of the DOPO-OH compound and thionyl chloride, so as to form the DOPO-C compound represented by formula (A) in the mixture.

The DOPO-C compound and the unreacted thionyl chloride were separated from the mixture by distillation, so as to obtain yellowish DOPO-C crude compound and the unreacted thionyl chloride separately, wherein the unreacted thionyl chloride could be reused. Pure DOPO-C compound was obtained by purifying the DOPO-C crude compound through reduced pressure distillation, and the obtained pure DOPO-C compound was grayish with a purity of 99.3%, which was determined by gas chromatography, and the yield was 92%.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A process for preparing 10-chloro-9,10-dihydro-9-oxa-10-phosphaphenanthrene-10-oxide (DOPO-C) compound, the process comprising steps of:
reacting a liquid chlorinating agent and 9,10-dihydro-10-hydroxy-9-oxa 10-phosphaphenanthrene 10-oxide (DOPO-OH) compound represented by formula (B) to form a mixture, wherein the mixture comprises DOPO-C compound represented by formula (A) and an unreacted liquid chlorinating agent,

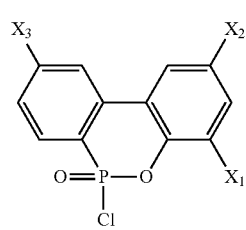

formula (A)

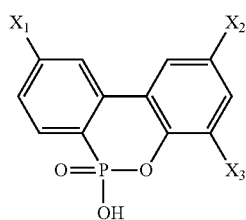

formula (B)

separating the DOPO-C compound represented by formula (A) and the unreacted liquid chlorinating agent from the mixture to obtain the DOPO-C compound represented by formula (A); wherein the variables $X_1$, $X_2$, and $X_3$ are each independently selected from the group consisting of hydrogen atom, hydroxyl group, cyano group, sulfonic acid group, sulfonate ester group represented by —$SO_3R_1$, halogen atom, alkoxy group represented by —$OR_2$, acyclic hydrocarbon group having 1 to 8 carbon atoms, cyclic alkyl group having 3 to 8 carbon atoms, aryl group, heteroaryl group, and arylalkyl group, wherein $R_1$ and $R_2$ are each independently an acyclic hydrocarbon group having 1 to 8 carbon atoms.

2. The process according to claim 1, wherein the liquid chlorinating agent is selected from the group consisting of thionyl chloride ($SOCl_2$), phosphorus oxychloride ($POCl_3$), phosphorus trichloride, ($PCl_3$), oxalyl chloride (($COCl_3$)$_2$), and a combination thereof.

3. The process according to claim 1, after the step of separating the DOPO-C compound represented by formula (A) and the unreacted liquid chlorinating agent from the mixture to obtain the DOPO-C compound represented by formula (A), the process comprises a step of re-purifying the DOPO-C compound represented by formula (A).

4. The process according to claim 1, wherein the step of reacting a liquid chlorinating agent and DOPO-OH compound to form a mixture includes reacting the liquid chlorinating agent and the DOPO-OH compound to form the mixture at a temperature ranging from 50° C. to 130° C.

5. The process according to claim 1, wherein an equivalent of the liquid chlorinating agent is at least 1/Y when the equivalent of the DOPO-OH compound is 1, wherein Y represents an equivalent of chlorine of the liquid chlorinating agent that react with one equivalent of the DOPO-OH compound.

6. The process according to claim 5, wherein the equivalent of the liquid chlorinating agent ranges from 1/Y to 10 when the equivalent of the DOPO-OH compound is 1.

7. The process according to claim 1, before the step of reacting a liquid chlorinating agent and DOPO-OH compound to form a mixture, the process comprises the steps of:
reacting water and 9,10-dihydro-9-oxa-10-phosphaphenanthrene-10-oxide (DOPO) compound to form an aqueous solution, wherein the DOPO compound is represented by formula (C);

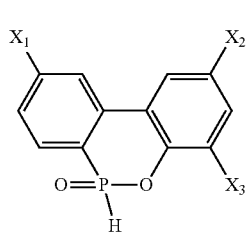

formula (C)

adding a metal-free oxidant into the aqueous solution to obtain a mixed solution, wherein the mixed solution comprises the DOPO-OH compound represented by formula (B); and separating the DOPO-OH compound represented by formula (B) from the mixed solution, so as to obtain the DOPO-OH compound; wherein the variables $X_1$, $X_2$, and $X_3$ are each independently selected from the group consisting of hydrogen atom, hydroxyl group, cyano group, sulfonic acid group, sulfonate ester group represented by —$SO_3R_1$, halogen atom, alkoxy group represented by —$OR_2$, acyclic hydrocarbon group having 1 to 8 carbon atoms, cyclic alkyl group having 1 to 8 carbon atoms, aryl group, heteroaryl group, and arylalkyl group, wherein $R_1$ and $R_2$ are each independently an acyclic hydrocarbon group having 1 to 8 carbon atoms.

8. The process according to claim 7, before the step of reacting water and DOPO compound to form an aqueous solution, the process comprises steps of: providing the DOPO compound; and heating the DOPO compound to a temperature ranging from 100° C. to 180° C. to render the DOPO compound in liquid form.

9. The process according to claim 7, wherein the step of reacting water and DOPO compound to form an aqueous solution includes reacting water and the DOPO compound to form an aqueous solution at a temperature ranging from 90° C. to 110° C.

10. The process according to claim 7, wherein the step of adding a metal-free oxidant into the aqueous solution to obtain a mixed solution includes adding a metal-free oxidant into the aqueous solution to obtain a mixed solution at a temperature ranging from 90° C. to 110° C.

11. The process according to claim 7, wherein the liquid chlorinating agent is thionyl chloride.

12. The process according to claim 7, wherein the metal-free oxidant is selected from the group consisting of hydrogen peroxide, oxygen, ozone, halogen, hypochloric acid, chloric acid, perchloric acid, peracetic acid, and a combination thereof.

13. The process according to claim 12, wherein the metal-free oxidant is hydrogen peroxide.

14. The process according to claim 2, before the step of reacting a liquid chlorinating agent and DOPO-OH compound to form a mixture, the process comprises the steps of:
reacting water and 9,10-dihydro-9-oxa-10-phosphaphenanthrene-10-oxide (DOPO) compound to form an aqueous solution, wherein the DOPO compound is represented by formula (C);

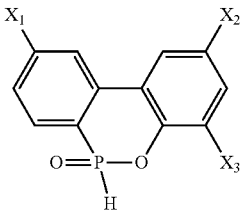

formula (C)

adding a metal-free oxidant into the aqueous solution to obtain a mixed solution, wherein the metal-free oxidant is free from metal element and the mixed solution comprises the DOPO-OH compound represented by formula (B); and separating the DOPO-OH compound represented by formula (B) from the mixed solution, so as to obtain the DOPO-OH compound; wherein the variables $X_1$, $X_2$, and $X_3$ are each independently selected from the group consisting of hydrogen atom, hydroxyl group, cyano group, sulfonic acid group, sulfonate ester group represented by —$SO_3R_1$, halogen atom, alkoxy group represented by —$OR_2$, acyclic hydrocarbon group having 1 to 8 carbon atoms, cyclic alkyl group having 3 to 8 carbon atoms, aryl group, heteroaryl group, and arylalkyl group, wherein $R_1$ and $R_2$ are each independently an acyclic hydrocarbon group having 1 to 8 carbon atoms.

15. The process according to claim 3, wherein before the step of reacting a liquid chlorinating agent and DOPO-OH compound to form a mixture, the process comprises the steps of:

reacting water and 9,10-dihydro-9-oxa-10-phosphaphenanthrene-10-oxide (DOPO) compound to form an aqueous solution, wherein the DOPO compound is represented by formula (C);

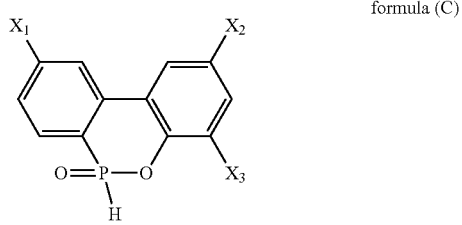

formula (C)

adding a metal-free oxidant into the aqueous solution, so as to obtain a mixed solution, wherein the metal-free oxidant is free from metal element and the mixed solution comprises the DOPO-OH compound represented by formula (B); and separating the DOPO-OH compound represented by formula (B) from the mixed solution, so as to obtain the DOPO-OH compound; wherein the variables $X_1$, $X_2$, and $X_3$ are each independently selected from the group consisting of hydrogen atom, hydroxyl group, cyano group, sulfonic acid group, sulfonate ester group represented by —$SO_3R_1$, halogen atom, alkoxy group represented by —$OR_2$, acyclic hydrocarbon group having 1 to 8 carbon atoms, cyclic alkyl group having 3 to 8 carbon atoms, aryl group, heteroaryl group, and arylalkyl group, wherein $R_1$ and $R_2$ are each independently an acyclic hydrocarbon group having 1 to 8 carbon atoms.

16. The process according to claim 4, wherein before the step of reacting a liquid chlorinating agent and DOPO-OH compound to form a mixture, the process comprises the steps of:

reacting water and 9,10-dihydro-9-oxa-10-phosphaphenanthrene-10-oxide (DOPO) compound to form an aqueous solution, wherein the DOPO compound is represented by formula (C);

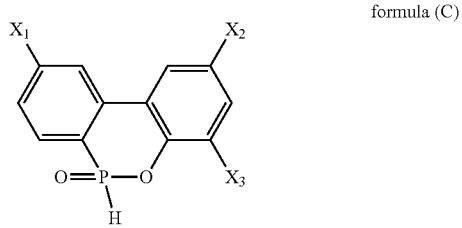

formula (C)

adding a metal-free oxidant into the aqueous solution, so as to obtain a mixed solution, wherein the metal-free oxidant is free from metal element and the mixed solution comprises the DOPO-OH compound represented by formula (B); and separating the DOPO-OH compound represented by formula (B) from the mixed solution, so as to obtain the DOPO-OH compound; wherein the variables $X_1$, $X_2$, and $X_3$ are each independently selected from the group consisting of hydrogen atom, hydroxyl group, cyano group, sulfonic acid group, sulfonate ester group represented by —$SO_3R_1$, halogen atom, alkoxy group represented by —$OR_2$, acyclic hydrocarbon group having 1 to 8 carbon atoms, cyclic alkyl group having 3 to 8 carbon atoms, aryl group, heteroaryl group, and arylalkyl group, wherein $R_1$ and $R_2$ are each independently an acyclic hydrocarbon group having 1 to 8 carbon atoms.

17. The process according to claim 5, before the step of reacting a liquid chlorinating agent and DOPO-OH compound to form a mixture, the process comprises the steps of:

reacting water and 9,10-dihydro-9-oxa-10-phosphaphenanthrene-10-oxide (DOPO) compound to form an aqueous solution, wherein the DOPO compound is represented by formula (C);

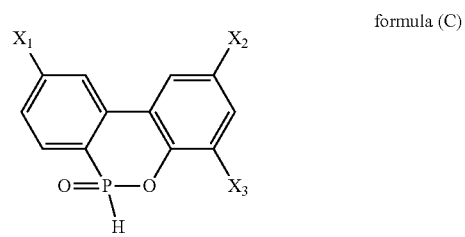

formula (C)

adding a metal-free oxidant into the aqueous solution, so as to obtain a mixed solution, wherein the metal-free oxidant is free from metal element and the mixed solution comprises the DOPO-OH compound represented by formula (B); and separating the DOPO-OH compound represented by formula (B) from the mixed solution, so as to obtain the DOPO-OH compound; wherein the variables $X_1$, $X_2$, and $X_3$ are each independently selected from the group consisting of hydrogen atom, hydroxyl group, cyano group, sulfonic acid group, sulfonate ester group represented by —$SO_3R_1$, halogen atom, alkoxy group represented by —$OR_2$, acyclic hydrocarbon group having 1 to 8 carbon atoms, cyclic alkyl group having 3 to 8 carbon atoms, aryl group, heteroaryl group, and arylalkyl group, wherein $R_1$ and $R_2$ are each independently an acyclic hydrocarbon group having 1 to 8 carbon atoms.

18. The process according to claim 6, before the step of reacting a liquid chlorinating agent and DOPO-OH compound to form a mixture, the process comprises the steps of:

reacting water and 9,10-dihydro-9-oxa-10-phosphaphenanthrene-10-oxide (DOPO) compound to form an aqueous solution, wherein the DOPO compound is represented by formula (C);

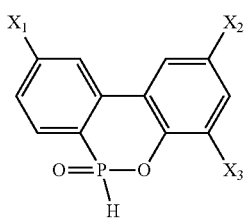

formula (C)

adding a metal-free oxidant into the aqueous solution, so as to obtain a mixed solution, wherein the metal-free oxidant is free from metal element and the mixed solution comprises the DOPO-OH compound represented by formula (B); and separating the DOPO-OH compound represented by formula (B) from the mixed solution, so as to obtain the DOPO-OH compound; wherein the variables $X_1$, $X_2$, and $X_3$ are each independently selected from the group consisting of hydrogen atom, hydroxyl group, cyano group, sulfonic acid group, sulfonate ester group represented by —$SO_3R_1$, halogen atom, alkoxy group represented by —$OR_2$, acyclic hydrocarbon group having 1 to 8 carbon atoms, cyclic alkyl group having 3 to 8 carbon atoms, aryl group, heteroaryl group, and arylalkyl group, wherein $R_1$ and $R_2$ are each independently an acyclic hydrocarbon group having 1 to 8 carbon atoms.

19. The process according to claim 18, before the step of reacting water and DOPO compound to form an aqueous solution, the process comprises steps of: providing the DOPO compound; and heating the DOPO compound to a temperature ranging from 100° C. to 180° C. to render the DOPO compound in liquid form.

20. The process according to claim 18, wherein the step of reacting water and DOPO compound to form an aqueous solution includes reacting water and the DOPO compound to form an aqueous solution at a temperature ranging from 90° C. to 110° C.

* * * * *